(«12») United States Patent
Jakkula et al.

(10) Patent No.: US 6,427,521 B2
(45) Date of Patent: *Aug. 6, 2002

(54) METHOD AND MEASURING ARRANGEMENT FOR MEASURING GAS CONTENT OF FLUID

(75) Inventors: Pekka Jakkula; Ilkka Dahlström; Timo Manninen, all of Oulu (FI)

(73) Assignee: Metso Field Systems Oy., Helsinki (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/346,431

(22) Filed: Jul. 1, 1999

(30) Foreign Application Priority Data

Jul. 10, 1998 (FI) .................................................. 981588

(51) Int. Cl.⁷ ........................................... G01N 33/497
(52) U.S. Cl. ................... 73/19.01; 324/613; 324/639
(58) Field of Search ..................... 73/19.01, 61.41, 73/61.43, 61.44, 861.04, 861.05; 324/637, 639, 613

(56) References Cited

U.S. PATENT DOCUMENTS

| | | | | |
|---|---|---|---|---|
| 4,683,759 A | * | 8/1987 | Skarsvaag et al. | 73/861.04 |
| 4,852,395 A | * | 8/1989 | Kolpak | 73/61.1 R |
| 5,051,922 A | * | 9/1991 | Toral et al. | 364/510 |
| 5,363,050 A | * | 11/1994 | Guo et al. | 324/638 |
| 5,485,743 A | * | 1/1996 | Taherian et al. | 73/61.44 |

(List continued on next page.)

FOREIGN PATENT DOCUMENTS

| | | |
|---|---|---|
| DE | 40 13 402 A1 | 11/1990 |
| EP | 0 436 286 A2 | 7/1991 |
| EP | 0 619 485 A1 | 10/1994 |
| FI | 84299 | 7/1991 |
| FI | 972172 | 11/1998 |
| JP | 5-322801 A | 12/1993 |
| JP | 4-238246 A | 1/1999 |
| SE | 505 241 C2 | 7/1997 |
| WO | WO 98/53306 A1 | 11/1998 |

OTHER PUBLICATIONS

Dykesteen, "Comparison of experiences from Multiphase Metering in different Operations", Feb. 1999, IBC conference on field applications & new technologies for multiphase metering.*

Amdal et al., "Handbook of multiphase metering", Feb. 1999, Produced for The Norwegian Society for Oil and Gas Measurement.*

The Scientist and Engineer's Guide to Digital Signal Processing by Steven W. Smith, California Technical Publishing, ISBN 0–9660176–3–3 (1997), Title Page, Chap. 1, (complete) and Chap. 15 pp. 277–279.*

The Scientist and Engineer's Guide to Digital Signal Processing by Steven W. Smith, California Technical Publishing, ISBN 0–9660176–3–3 (1997).*

*Primary Examiner*—Hezron Williams
*Assistant Examiner*—C D Garber
(74) *Attorney, Agent, or Firm*—Alston & Bird LLP

(57) ABSTRACT

The invention relates to a method and a measuring arrangement for measuring the gas content of a fluid (13). The fluid (13) comprises gas bubbles. In the method, microwave radiation (20) is transmitted through the fluid (13) and a signal (7) indicating the travel time, phase or amplitude of the radiation (20) is formed in a microwave measuring device (16), and a gas measuring equipment (18) determines the gas content of the fluid (13) by means of the signal (7).

25 Claims, 4 Drawing Sheets

U.S. PATENT DOCUMENTS

| | | | | |
|---|---|---|---|---|
| 5,502,393 A | * | 3/1996 | Yamaguchi et al. | 324/639 |
| 5,581,191 A | * | 12/1996 | Yamaguchi | 324/637 |
| 5,596,150 A | * | 1/1997 | Arndt et al. | 73/861.12 |
| 5,625,293 A | * | 4/1997 | Marrelli et al. | 324/638 |
| 5,701,083 A | * | 12/1997 | Goldberg et al. | 324/642 |
| 5,714,691 A | * | 2/1998 | Hill | 73/861.04 |
| 5,741,979 A | * | 4/1998 | Arndt et al. | 73/861.05 |
| 5,741,980 A | * | 4/1998 | Hill et al. | 73/861.04 |
| 5,864,240 A | * | 1/1999 | Hirai et al. | 324/639 |
| 5,869,771 A | * | 2/1999 | Rajan et al. | 73/861.04 |
| 6,012,324 A | * | 1/2000 | Jakkula et al. | 73/19.03 |
| 6,028,307 A | * | 2/2000 | Young et al. | 250/256 |
| 6,155,102 A | * | 12/2000 | Toma et al. | 73/61.44 |
| 6,234,030 B1 | * | 5/2001 | Butler | 73/861.04 |
| 6,236,948 B1 | * | 5/2001 | Eck et al. | 702/45 |

* cited by examiner

METHOD AND MEASURING ARRANGEMENT FOR MEASURING GAS CONTENT OF FLUID

FIELD OF THE INVENTION

The invention relates to a method for measuring the gas content of a fluid, which comprises gas bubbles, in which method microwave radiation is transmitted through the fluid.

The invention also relates to a measuring arrangement for measuring the gas content of a fluid, which comprises gas bubbles, the measuring arrangement being arranged to transmit microwave radiation through the fluid, and comprising a transmitting antenna, a receiving antenna and a microwave measuring device, which are arranged to measure at least one variable of the microwave signal as the signal travels through the fluid.

BACKGROUND OF THE INVENTION

At present, the gas content and especially the air content of a fluid or a liquid substance are measured mainly by means of methods and devices based on the ultrasound and the measurement of density. Attenuation of the ultrasound is a function of the gas content of a fluid: the higher the gas content the greater the attenuation of the ultrasound. In the paper industry, the gas content of papermaking pulp is typically measured by means of the ultrasound. The quality of the final product, i.e. paper, depends on the quality of the liquid pulp, which, in turn, is partly dependent on the gas content thereof.

Finnish Patent 84,299 discloses an arrangement where the air content of a suspension is determined by measuring its water content at two different known pressures. Also American Patent 4,852,395 discloses an arrangement where the gas content of a flowing fluid is determined by measuring the transmissivity of microwave radiation through the fluid at two different known pressures.

The prior art also includes a gas measuring device comprising means for determining the gas content of a fluid based on changes caused by pressure variation in the variable of a microwave signal, This arrangement is described in greater detail in Finnish Patent 972,172, which is incorporated herein by reference.

However, a problem with gas content measurement based on the attenuation of the ultrasound is that the method cannot be applied in suspensions with a high percentage of solids. It is also difficult to apply the method to in-line-type assembly. A problem with density measurement, in turn, is that the measurement is highly sensitive to also other factors changing the concentration than just air, which is the most common gas in papermaking pulp.

The problem with microwave measurements carried out at two known pressures is that the pressures used in the measurements must be measured accurately from the very point where the microwave measurement is to be performed. The pressure indicator must be accurately calibrated in order to avoid systematic measurement errors in the gas content.

The problem with the arrangement disclosed in Finnish Patent 972,172 is that it is particularly difficult to accurately measure high gas contents.

BRIEF DESCRIPTION OF THE INVENTION

An object of the invention is to provide a method and an arrangement implementing the method with which the aforementioned problems can be solved. This is achieved with a method of the type described in the introduction, which is characterized by measuring at least one variable of the microwave radiation after the radiation has propagated through the fluid, and determining the gas content of the fluid on the basis of changes caused by the gas bubbles in the variable of the microwave radiation.

The arrangement according to the invention is characterized in that the measuring arrangement comprises a gas measuring equipment for determining the gas content of the fluid on the basis of changes caused by the gas bubbles in the variable of the microwave signal.

The method and the arrangement according to the invention provide several advantages. The gas content of a fluid can be measured regardless of the consistency of the substance. The exact pressure value or even information about pressure variations is not required. Especially in measurements carried out in the paper industry, the measurement according to the invention is insensitive to other factors than the gas content.

BRIEF DESCRIPTION OF THE FIGURES

In the following, the invention will be described in greater detail in connection with preferred embodiments with reference to the accompanying drawings, in which.

DETAILED DESCRIPTION OF THE INVENTION

The invention is applicable for measurement of the gas content of different flowing fluids and suspensions. The invention is particularly applicable for use in the manufacture of paper without being limited thereto, however.

Figure 1:
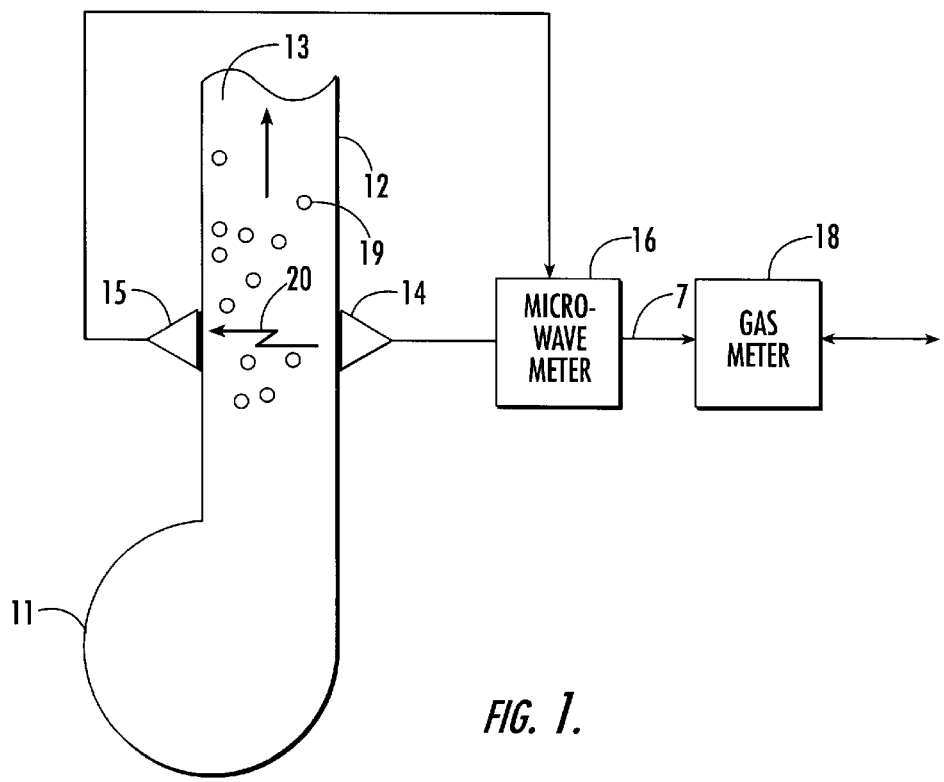
FIG. 1 shows a measuring arrangement employing phase measurement.

Let us examine the method according to the invention and a typical measuring arrangement implementing the method by means of FIG. 1. The arrangement of FIG. 1 comprises a pump 11, a duct 12, a fluid 13, a transmitter 14, a receiver 15, a microwave measuring device 16 and means 18 for determining the gas content. In the present application, the fluid 13 refers to any liquid substance which may flow in a pipe, in particular, such as a suspension, slurry, phase mixture or papermaking pulp. The pump 11 pumps the fluid 13, which thereafter flows in the duct 12. The operation of the pump 11 typically mixes the fluid 13 to such an extent that gas bubbles 19 mixed within the fluid 13 are rather evenly distributed. In a typical fluid 13, such as a suspension comprising wood fibres in water, no other components or particles but gas differ substantially from each other with respect to the dielectric constant. Water dielectric constant is $\epsilon_r=79$ and the dielectric constant of pulp flocs is $\epsilon_r=75.3$, whereas air dielectric constant is $\epsilon_r=1$. Since the air dielectric constant differs to such an extent from water and pulp, the air bubbles 19 cause a great deal of variation in the travel time of an electromagnetic signal and particularly a microwave signal, which can be detected, for example, as variation in the phase signal.

In the arrangement according to the invention, the electromagnetic radiation is preferably microwave radiation. In the case of microwave technology, the transmitter 14 is a prior art transmitting antenna for a microwave signal. Similarly, the receiver 15 is a prior art receiving antenna. A microwave signal 20 transmitted by the antenna 14 travels through the fluid 13 to the receiving antenna 15. The measuring device 16 measures the travel time of the microwave signal or, more preferably, the phase of the microwave radiation 20. In the inventive arrangement, it is possible to also measure the amplitude of the microwave radiation. Measurement of the absolute travel time is not essential in the inventive arrangement, but it is more important to measure the changes in the travel time. The microwave measuring device 16 forms, for example, a phase signal 7, and the measuring equipment 18 determines the gas content based on the variation in the phase signal. The measurement may be based on standard deviation, variance or the greatest deviation of the signal 7. The measuring equipment 18 preferably determines the change of the gas content compared to a known gas content. In order to measure an absolute gas content, the pressure must also be measured with prior art pressure indicators. The gas content must also be calibrated by means of prior art gas measuring equipments. The measurement result can be improved through filtration. It is possible, for example, to form an average of several measurement results. Further, the greatest deviations from the average can be rejected when the measurement results are being processed.

Figure 2:
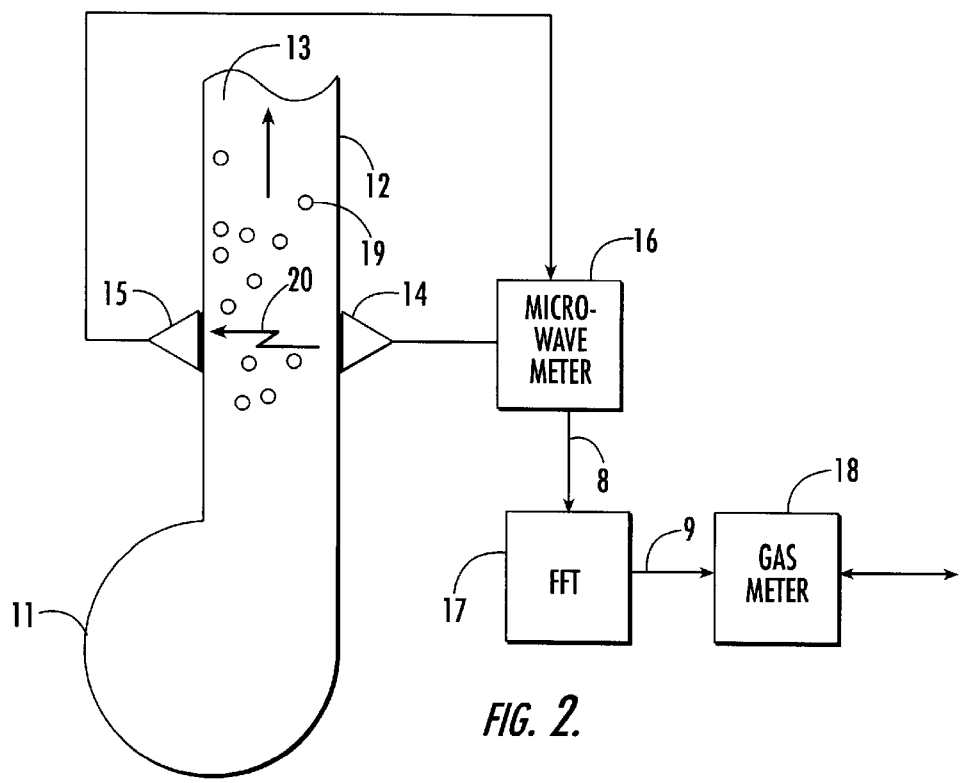
FIG. 2 shows a measuring arrangement employing the Fourier transform.
Figure 3:
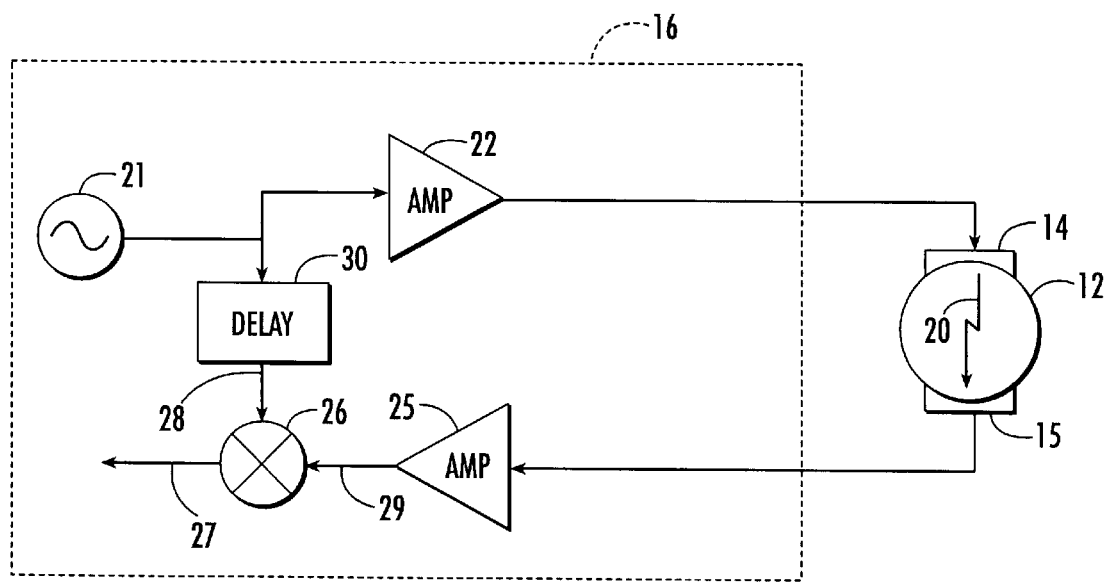
FIG. 3 shows a measuring arrangement for a phase of a microwave signal.

FIG. 2 shows another preferred embodiment of the invention. The microwave measuring device 16 transmits microwave radiation 20 with the transmitting antenna 14 through a fluid 13 to the receiving antenna 15. A signal 8 formed in the microwave measuring device 16 and related to the travel time, for example a phase signal or a signal measuring the intensity or attenuation of the microwave radiation 20, is subjected to the Fourier transform in means 17 to convert it into a signal 9 of the transform domain, which is supplied to the measuring equipment 18 for the determination of the gas content. The transformed signal S is supplied to the gas measuring equipment 18, which determines the gas content by means of the greatest value, effective value or area of the signal 9. In this embodiment the measurement result can also be improved through filtration both before and after the Fourier transform. It is possible, for example, to form an average of several measurement results. Further, the greatest deviations from the average can be rejected when the measurement results are being processed, Examine in greater detail by means of FIG. 3 an example of an arrangement according to the invention based on measurement of the phase of a microwave signal which has passed through the fluid 13. The arrangement related to the microwave measuring device 16 comprises a local oscillator 21, a transmitter amplifier 22, a receiver amplifier 25 and a mixer 26. The figure also shows the transmitting antenna 14, the duct 12 and the receiving antenna 15. The oscillator 21 transmits a microwave frequency to both the transmitter amplifier 22 and the mixer 26. After the transmitter amplifier 22 has amplified the signal of the oscillator 21, it travels to the actual process measurement carried out in the duct 12. When the signal has passed through the actual process measurement in parts 14, 12 and 15, it is forwarded to the receiver amplifier 25, From the receiver amplifier 25 the signal travels to the mixer 26, where the received signal 29 is multiplied by the original signal arriving from the oscillator 21 and delayed in a delay block 30. If the signals to be multiplied have a phase difference of 90°, the signal at the mixer output is set to zero. If, on the other hand, the phase difference is other than 90°, the phase difference signal 27 is other than zero and the magnitude of the signal 27 depends on the gas content When the gas content is being measured, such a frequency is preferably located by the oscillator 21 that the output signal 27 of the mixer 26 is substantially set to zero, whereupon the phase difference of a reference microwave signal 28 and the received microwave signal 29 is at least momentarily 90°. In such a situation, the oscillator 21 is preferably controlled by means of the signal 27. In the arrangement according to the invention, this frequency is set as the fixed frequency of the microwave signal, and changes in the travel time are measured by means of the phase difference between the reference signal 28 indicated by the output signal 27 of the mixer 26, and the received microwave signal 29. The gas content is preferably measured from the output signal 27 of the mixer 26 or from a phase signal formed from the output signal 27 and subjected to the Fourier transform.

Figure 4:
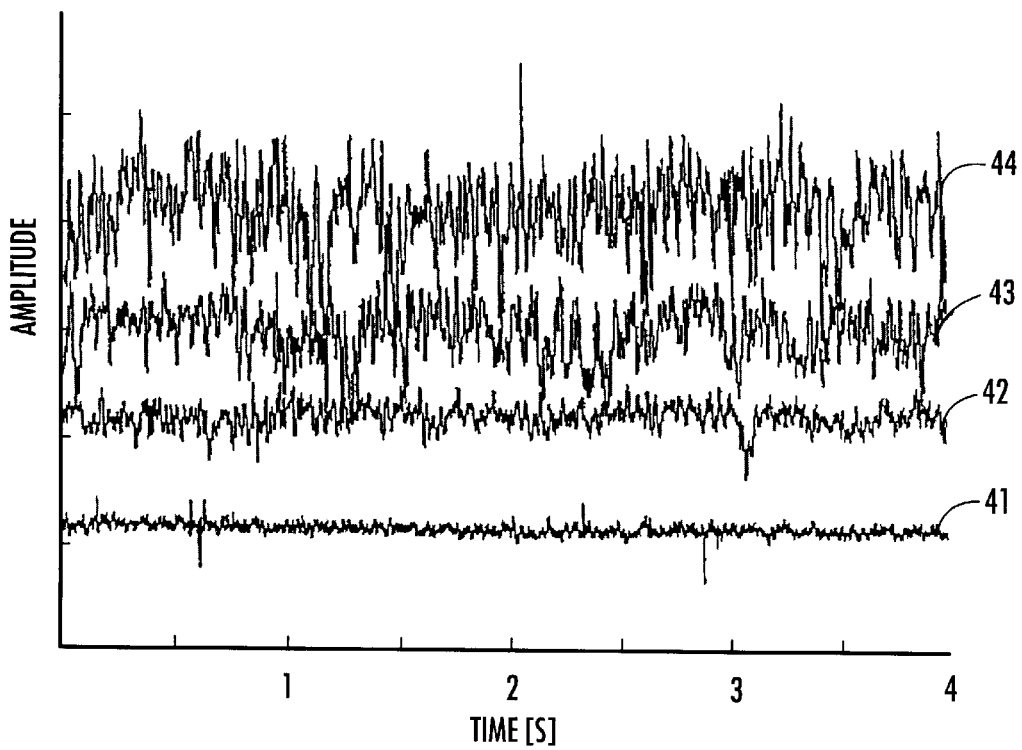
FIG. 4 shows a phase signal on the time domain with different air contents of water.

FIG. 4 shows the behaviour of a phase signal of microwave radiation with different air contents of water. The vertical axis denotes the amplitude of the phase signal on a freely selected scale, The horizontal axis denotes time in the range of 1–4 s. Curve 41 shows a situation with a low air content in the water. The amplitude of the oscillation of the phase signal resembling noise is very low. In the situation described by curve 42, the air content of water is higher and therefore the oscillation of the phase signal is stronger. In the situation described by curve 43, the air content is rather high and the oscillation is also stronger than previously. When there air content is as high as in the situation shown by curve 44, the oscillation of the phase signal is significant. The amount of air thus correlates with the amplitude of oscillation of the phase signal.

Figure 5A:
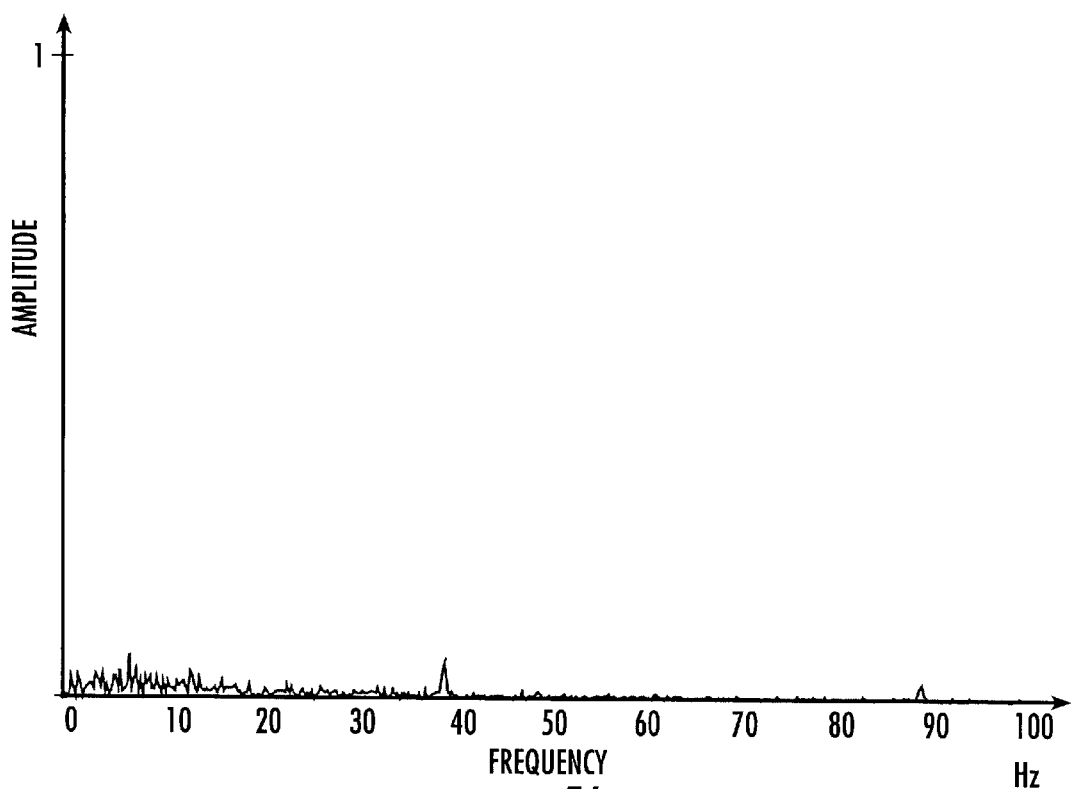
FIG. 5A shows a phase signal as a function of frequency in water with a low air content.
Figure 5B:
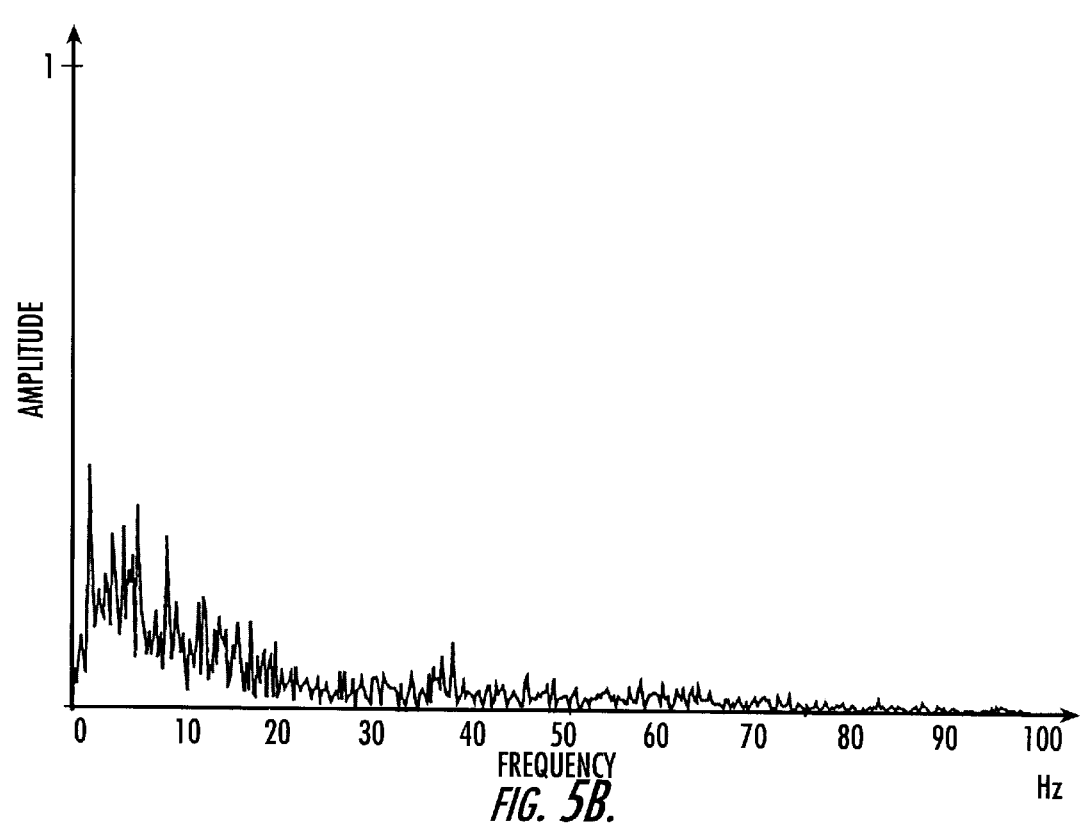
FIG. 5B shows a phase signal as a function of frequency in water with an average air content.
Figure 5C:
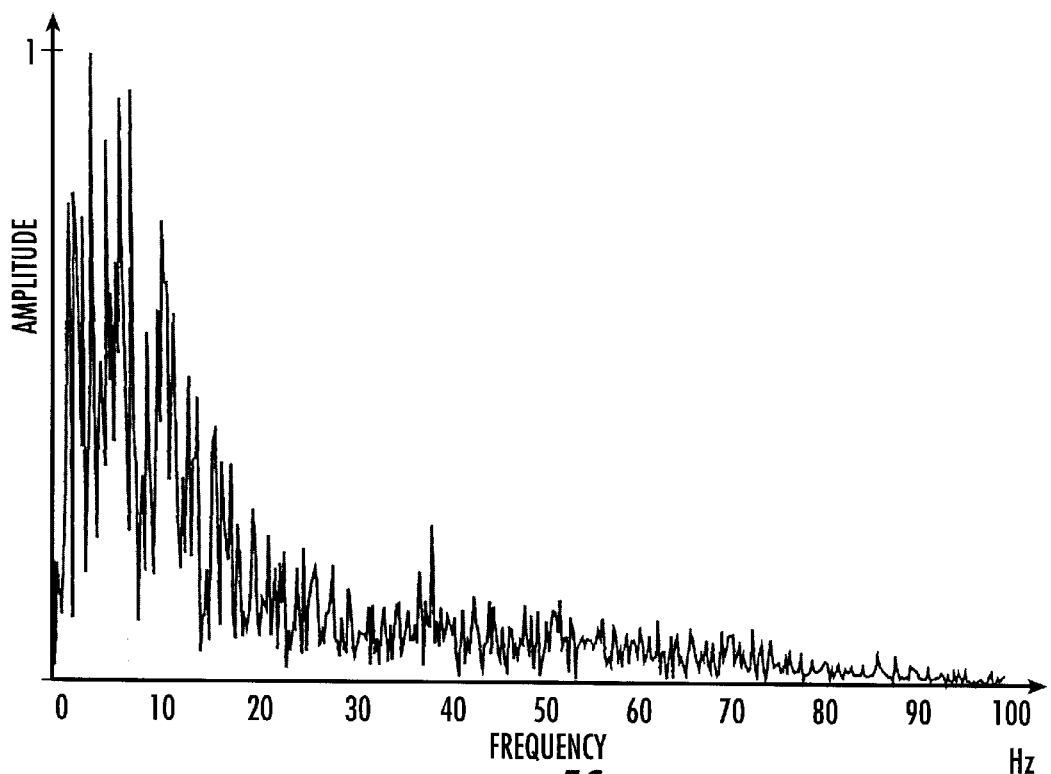
FIG. 5C shows a phase signal as a function of frequency in water with a high air content.

FIGS. 5A to 5C show measurement results when the phase of the microwave signal is examined on the frequency domain. The horizontal axis shows the frequency in the range of 0–100 Hz. The vertical axis is on the same scale in all three FIGS. 5A to 5C, and value 1 of the vertical axis denotes the greatest value of noise with the highest air content. A measurement signal, in this case the phase signal, related to the travel time of the received signal is subjected to the Fourier transform in a known manner in the means 17, The Fourier transform is calculated as an integral in the general form as follows:

$$F\{f(t)\} = F(\omega) = \frac{1}{\sqrt{2\pi}} \int_{-\infty}^{\infty} f(t) e^{-i\alpha x} dt,$$

wherein $F\{f(t)\}$ denotes the Fourier transform from function $f(t)$, $f(t)$ is a function of time t, $F(\omega)$ is a function subjected to the Fourier transform, $\omega$ is a frequency variable, i is an imaginary unit, and $\pi$ is pi. The Fourier transform integral is calculated in a digital system through summing which includes N terms to be summed. However, the number of operations in the FFT (Fast Fourier Transform) is reduced considerably. The Fourier transform usually requires a number $W^2$ of operations, but the FFT can be carried out preferably with a number $w^*\log_2(W)$ of operations (the Danielson-Lanczos theorem), where W denotes the number of elements in the transform.

In the microwave measurement according to the invention, small air bubbles cause low-frequency noise, which increases with the air content of the fluid 13. The fluid 13 should preferably be flowing or otherwise sufficiently mixed, as in the measurement of papermaking pulp, for example. When the fluid is water, the phenomenon is based on differences between the dielectric constants of gas, which is often air (air $\epsilon_r=1$), and water (water $\epsilon_r=79$). FIGS. 5A to 5C show the pressure variation produced by the pump, which has a narrow frequency band, substantially only one frequency component. In this case, the frequency component produced by the pump is at 40 Hz. On the frequency caused by the pump, the amplitude of the phase signal subjected to the Fourier transform depends on the amount of air, as shown in FIGS. 5A to 5C. However, with greater air contents (over 0.1%) the amount of gas or air in the fluid correlates better with the amplitude of the low-frequency noise than with the frequency caused by the pump. The frequency band of the noise caused by the air bubbles is wide and differs thus clearly from the single frequency component produced by the pump. In the situation shown in FIG. 5A, the air content of water is low, in the situation shown in FIG. 5B the air content of water is higher, and in the situation shown in FIG. 5C the air content of water is high.

Figure 6:
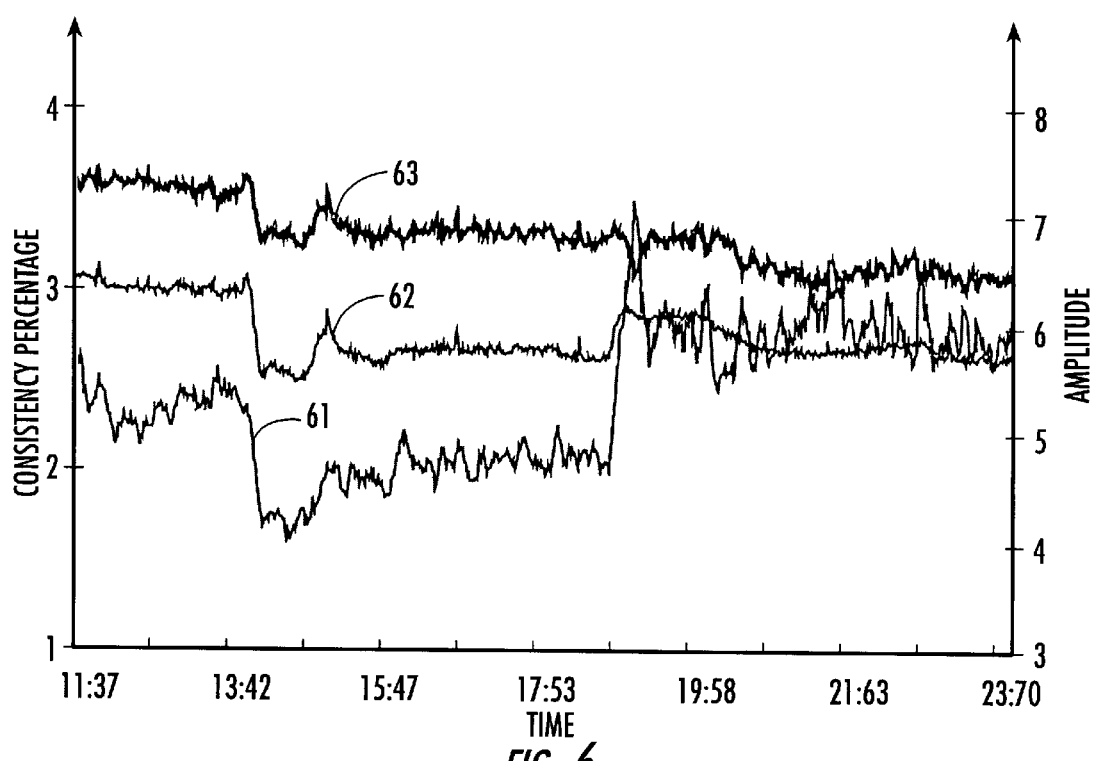
FIG. 6 shows how the measurement of the gas content compensates for the measurement of the consistency.

By means of the gas content measurement according to the invention it is possible to correct the result of the consistency measurement if the result is also a function of the gas content, as it is at least in measurements of consistency based on microwave technique and radioactivity. FIG. 6 shows three curves, wherein curve 61 is a phase signal, curve 62 is a consistency curve and curve 63 is a corrected consistency curve, The vertical axis on the left side of the figure shows the consistency in the range 1%–4%. The vertical axis on the right side of the figure comprises the values of the phase signal on a freely selected scale from 3 to 8. The horizontal axis shows the time. The measurements have been carried out on papermaking pulp where the effective air content has been suddenly reduced by raising the pressure. When the effective air content has been changed in the point indicated by reference numeral 61, also the device which measures the consistency, based on microwave technology, has reacted to the change as if the consistency had decreased. The result of the consistency measurement can be corrected by deleting therefrom the effective gas content. The consistency result that has been corrected in such a manner is described by curve 63.

The fluid 13 in the arrangement according to the invention is preferably papermaking pulp in a process pipe, and the method according to the invention is used to measure the gas content of the pulp before the pulp is supplied to the paper machine in order to improve the quality of the paper. The arrangement according to the invention can be used either alone or together with some other gas measuring equipment. The arrangement according to the invention can be implemented by means of prior art optical or radiotechnical components. The Fourier transformer 17 and the gas measurement block 18 can be implemented most preferably by means of microprocessor and digital technology and a suitable program which performs the required process steps.

Even though the invention is described above with reference to an example according to the accompanying drawings, it is clear that the invention is not restricted thereto but it can be modified in several ways within the scope of the inventive idea disclosed in the appended claims.

What is claimed is:

1. A method for measuring the gas content of a fluid, which has gas bubbles, in which method microwave radiation is transmitted through the fluid, the method comprising the steps of:

measuring at least one variable of the microwave radiation after the radiation has propagated through the fluid, and determining the gas content of the fluid on the basis of noise caused by gas bubbles in the variable of the microwave radiation.

2. A method according to claim 1, wherein said measuring step determine the change in travel time of the propagation of the microwave radiation through the fluid by measuring a change in at least one variable of the microwave radiation.

3. A method according to claim 2, wherein the variable of the microwave radiation is the phase.

4. A method according to claim 1, wherein the variable of the microwave radiation is the amplitude of the radiation.

5. A method according to claim 1, wherein a variable signal is formed form the changes of the variable of the microwave radiation, and the variable signal is filtered in order to make the gas content measurement more accurate.

6. A method according to claim 5, wherein the variable signal is filtered by averaging in order to make the gas content measurement more accurate.

7. A method according to claim 1, wherein the gas content is determined by means of a value describing the changes in the variable.

8. A method according to claim 1, wherein the value describing the changes is one of a standard deviation and variance.

9. A method according to claim 1, wherein the value describing the changes is the greatest value of the change.

10. A method according to claim 1, wherein said measuring step further comprises the steps of:

forming the measured variable of the microwave radiation into a measurement signal;

converting the measurement signal from the time domain into the transform domain;

forming a value that is characteristic of the transformed signal; and forming the gas content of the fluid by means of the value characteristic of the transformed signal.

11. A method according to claim 10, wherein the characteristic value is one of the greatest value, effective value, and area of the signal.

12. A method according to claim 1, wherein the consistency of the fluid is also measured, the result of the consistency measurement is corrected according to the result of the gas content measurement.

13. A method according to claim 1, wherein the fluid in the method is papermaking pulp, and the method is applied in the measurement for air content which is about 0.1% or more of the total volume of the pulp.

14. A measuring arrangement for measuring the gas content of a fluid, which has gas bubbles, the measuring arrangement being arranged to transmit microwave radiation through the fluid, and comprising a transmitting antenna, a receiving antenna and a microwave measuring device, which are arranged to measure at least one variable of the microwave signal as the signal travels through the fluid, wherein the measuring arrangement comprises a gas measuring equipment for determining the gas content of the fluid on the basis of noise caused by the gas bubbles in the variable of the microwave signal.

15. A measuring arrangement according to claim 14, wherein the variable of the microwave radiation is the phase.

16. A measuring arrangement according to claim 14, wherein the variable of the microwave radiation is the travel time.

17. A measuring arrangement according to claim 14, wherein the variable of the microwave radiation is the amplitude of the radiation.

18. A measuring arrangement according to claim 14, wherein the microwave measuring device is arranged to form a variable signal and to filter the signal in order to make the gas content measurement more accurate, and to supply the filtered variable signal to the measuring equipment.

19. A measuring arrangement according to claim 18, wherein the microwave measuring device filters the signal through averaging in order to make the gas content measurement more accurate.

20. A measuring arrangement according to claim 14, wherein the gas measuring equipment is arranged to determine the gas content by means of a value describing the changes in the variable.

21. A measuring arrangement according to claim 20, wherein the value describing the changes is one of a standard deviation and variance.

22. A measuring arrangement according to claim 14, wherein the microwave measuring device is arranged to form a measurement signal from the variable, the measuring arrangement comprising:

transform means for transforming the measurement signal from the time domain into the transform domain; and gas measuring means equipment, which is arranged to form a value that is characteristic of the transformed signal, and to form the gas content of the fluid by means of the value characteristic of the transformed signal.

23. A measuring arrangement according to claim 22, wherein the characteristic value is one of the greatest value, effective value, and area of the signal.

24. A measuring arrangement according to claim 14, wherein, when the consistency of the fluid is also measured, the gas measuring equipment is arranged to correct the result of the consistency measurement by means of the result of the gas content measurement.

25. A method according to claim 14, wherein the measuring arrangement is arranged to measure papermaking pulp as the fluid, and the measuring arrangement is arranged to measure air content which is about 0.1% or more of the total volume of the pulp.

* * * * *